United States Patent
Clair et al.

(10) Patent No.: US 9,138,530 B2
(45) Date of Patent: Sep. 22, 2015

(54) CATHETER ASSEMBLY AND METHOD OF TREATING A VASCULAR DISEASE

(71) Applicant: THE CLEVELAND CLINIC FOUNDATION, Cleveland, OH (US)

(72) Inventors: Daniel G. Clair, Shaker Heights, OH (US); Shubhayu Basu, Solon, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 29 days.

(21) Appl. No.: 13/768,205

(22) Filed: Feb. 15, 2013

(65) Prior Publication Data

US 2013/0211379 A1     Aug. 15, 2013

Related U.S. Application Data

(60) Provisional application No. 61/598,979, filed on Feb. 15, 2012, provisional application No. 61/752,061, filed on Jan. 14, 2013.

(51) Int. Cl.
*A61B 18/00*     (2006.01)
*A61M 5/00*     (2006.01)
(Continued)

(52) U.S. Cl.
CPC .............. *A61M 5/00* (2013.01); *A61B 17/22012* (2013.01); *A61B 18/1492* (2013.01); *A61B 18/22* (2013.01); *A61B 18/24* (2013.01);
(Continued)

(58) Field of Classification Search
CPC .................. A61M 5/187; A61B 18/00; A61B 2017/00867; A61B 2019/5427; A61B 25/0068; A61B 2025/0087; A61B 2025/0096

USPC .............. 604/64.13, 95.01, 96.01, 158, 187, 604/164.01, 164.04, 164.06, 164.07, 164.1, 604/165.01, 166.01, 272, 95.05, 264, 528
See application file for complete search history.

(56) References Cited

U.S. PATENT DOCUMENTS

| | | | |
|---|---|---|---|
| 4,578,061 | A | 3/1986 | Lemelson |
| 5,112,305 | A | 5/1992 | Barath et al. |

(Continued)

FOREIGN PATENT DOCUMENTS

| | | |
|---|---|---|
| WO | 2007002304 A2 | 1/2007 |
| WO | 2008020967 A2 | 2/2008 |
| WO | 2008115566 A2 | 9/2008 |

OTHER PUBLICATIONS

PCT International Search Report and Written Opinion for PCT/US2013/026315, mailed May 29, 2013, pp. 1-13.

*Primary Examiner* — Scott Medway
(74) *Attorney, Agent, or Firm* — Tarolli, Sundheim, Covell & Tummino LLP

(57) ABSTRACT

A catheter assembly comprises a catheter including a catheter wall and a lumen extending lengthwise of the wall. The wall has inner and outer surfaces. The wall includes plural openings that extend through the wall and communicate with the lumen. An elongated hollow needle includes a proximal end portion and a distal end portion. The needle is movable in the lumen to move the distal end portion between the openings. The distal end portion is directed radially outward so as to extend into an adjacent opening. The distal end portion has a configuration that stores potential energy when in the lumen. The potential energy is converted to kinetic energy to produce movement of the proximal end portion as the distal end portion moves from the inner surface of the catheter wall across an edge of an opening. The movement of the proximal end portion is haptically perceptible.

16 Claims, 7 Drawing Sheets

(51) Int. Cl.
  *A61M 25/00* (2006.01)
  *A61B 18/14* (2006.01)
  *A61B 18/24* (2006.01)
  *A61B 17/22* (2006.01)
  *A61B 18/22* (2006.01)
  *A61M 25/01* (2006.01)
  *A61B 18/18* (2006.01)

(52) U.S. Cl.
  CPC .. *A61M25/0084* (2013.01); *A61B 2018/00029* (2013.01); *A61B 2018/00285* (2013.01); *A61B 2018/00297* (2013.01); *A61B 2018/00309* (2013.01); *A61B 2018/00404* (2013.01); *A61B 2018/1475* (2013.01); *A61B 2018/1807* (2013.01); *A61B 2218/002* (2013.01); *A61M 25/0026* (2013.01); *A61M 25/0108* (2013.01); *A61M 2025/0059* (2013.01); *A61M 2025/0086* (2013.01); *A61M 2025/0092* (2013.01)

(56) References Cited

U.S. PATENT DOCUMENTS

| | | | |
|---|---|---|---|
| 5,284,476 A * | 2/1994 | Koch | 604/274 |
| 5,292,311 A | 3/1994 | Cope | |
| 5,354,279 A | 10/1994 | Hofling | |
| 5,360,416 A | 11/1994 | Ausherman et al. | |
| 5,499,975 A | 3/1996 | Cope et al. | |
| 5,693,029 A | 12/1997 | Leonhardt | |
| 5,769,868 A | 6/1998 | Yock | |
| 6,102,904 A | 8/2000 | Vigil et al. | |
| 6,283,951 B1 | 9/2001 | Flaherty et al. | |
| 6,302,870 B1 | 10/2001 | Jacobsen et al. | |
| 6,425,887 B1 | 7/2002 | McGuckin et al. | |
| 6,447,477 B2 | 9/2002 | Burney et al. | |
| 6,685,648 B2 | 2/2004 | Flaherty et al. | |
| 6,692,466 B1 | 2/2004 | Chow et al. | |
| 6,905,480 B2 * | 6/2005 | McGuckin et al. | 604/164.01 |
| 6,926,692 B2 | 8/2005 | Katoh et al. | |
| 6,989,004 B2 * | 1/2006 | Hinchliffe et al. | 604/164.01 |
| 7,070,606 B2 | 7/2006 | Seward | |
| 7,127,284 B2 | 10/2006 | Seward | |
| 7,141,041 B2 | 11/2006 | Seward | |
| 7,163,533 B2 | 1/2007 | Hobbs et al. | |
| 7,172,576 B2 | 2/2007 | Sawa et al. | |
| 7,377,910 B2 | 5/2008 | Katoh et al. | |
| 7,381,200 B2 | 6/2008 | Katoh et al. | |
| 7,465,298 B2 | 12/2008 | Seward et al. | |
| 7,691,080 B2 | 4/2010 | Seward et al. | |
| 7,744,584 B2 | 6/2010 | Seward et al. | |
| 7,879,011 B2 | 2/2011 | Chang | |
| 8,500,697 B2 * | 8/2013 | Kurth et al. | 604/170.03 |
| 2002/0143302 A1 | 10/2002 | Hinchliffe et al. | |
| 2005/0096629 A1 * | 5/2005 | Gerber et al. | 604/506 |
| 2005/0228452 A1 | 10/2005 | Mourlas et al. | |
| 2006/0095015 A1 | 5/2006 | Hobbs et al. | |
| 2006/0293647 A1 | 12/2006 | McRae et al. | |
| 2007/0129706 A1 | 6/2007 | Katoh et al. | |
| 2007/0299404 A1 | 12/2007 | Katoh et al. | |
| 2008/0294096 A1 | 11/2008 | Uber, III et al. | |
| 2009/0312617 A1 | 12/2009 | Creed et al. | |
| 2012/0323220 A1 | 12/2012 | Mackay, II et al. | |

\* cited by examiner

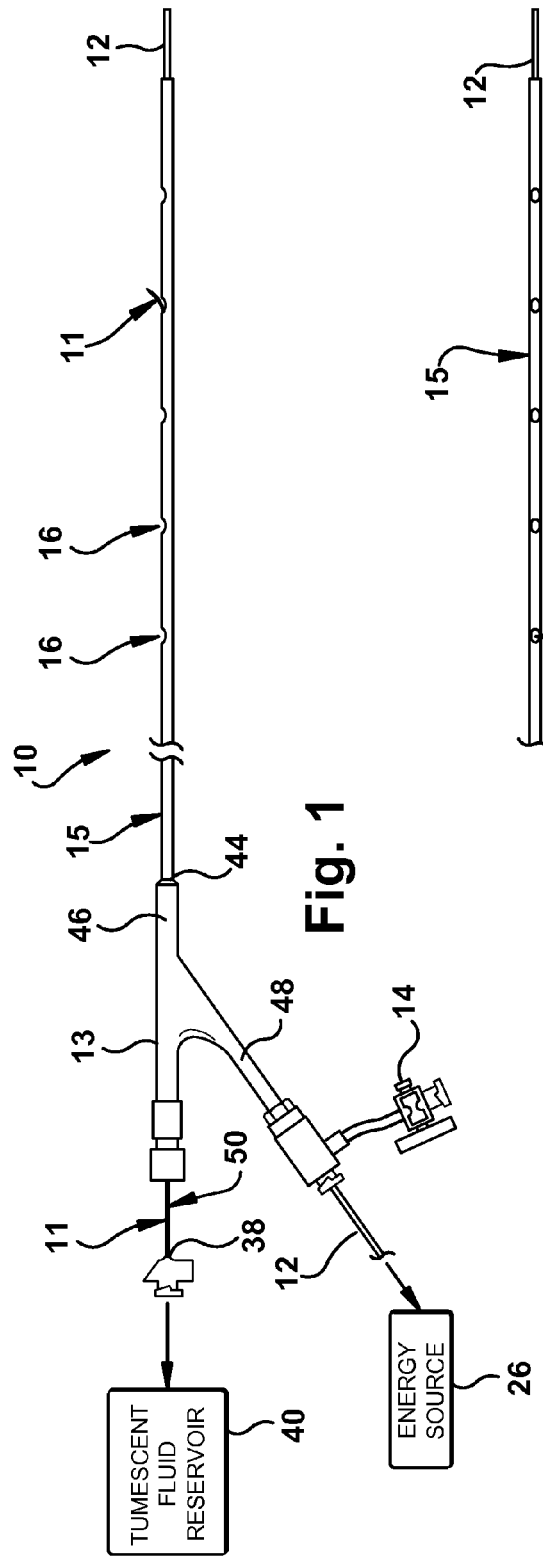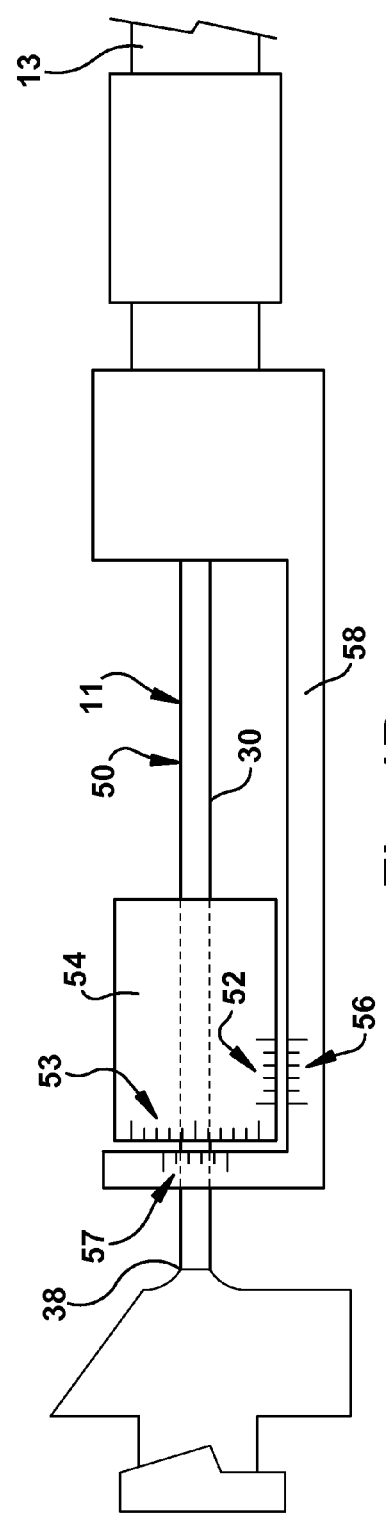

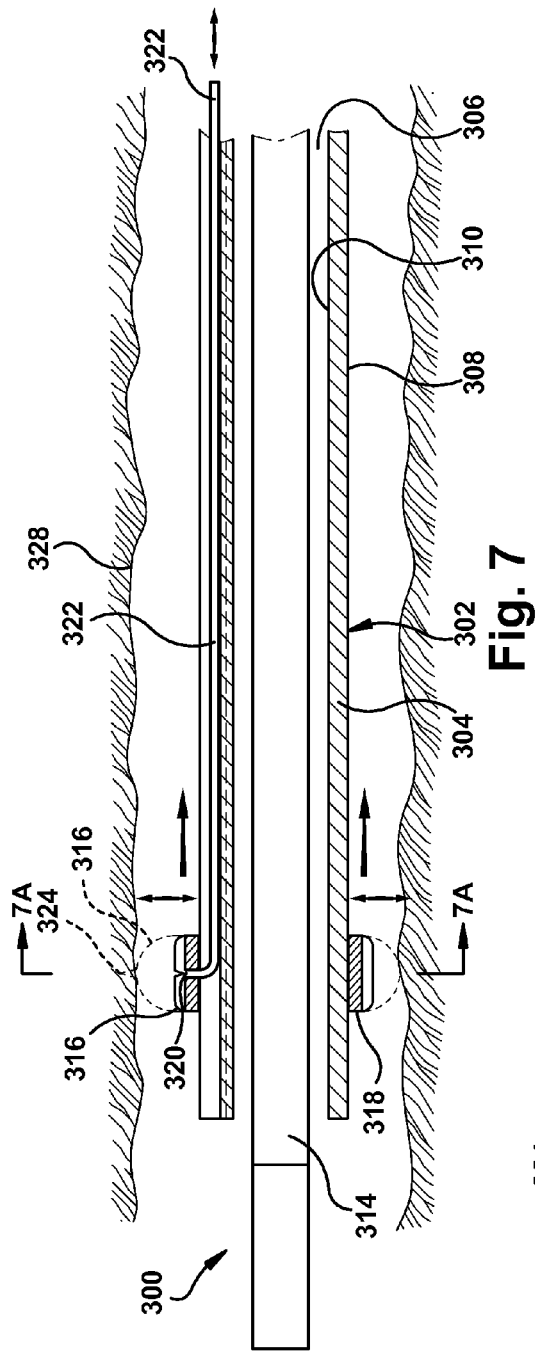
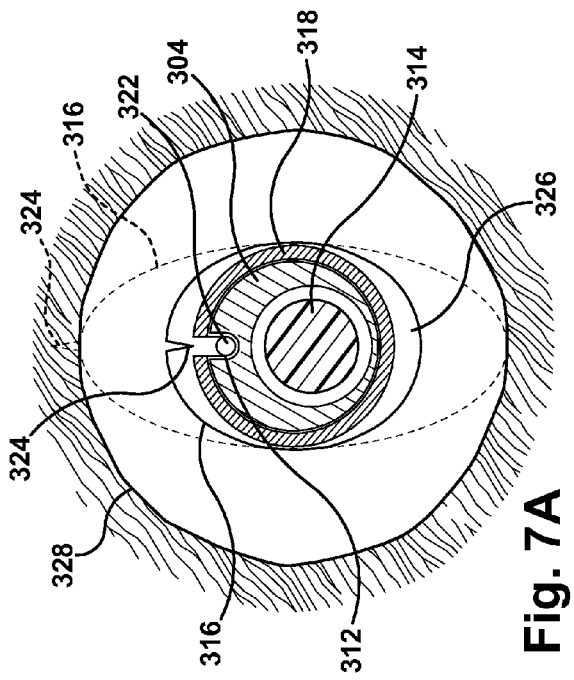

CATHETER ASSEMBLY AND METHOD OF TREATING A VASCULAR DISEASE

CROSS-REFERENCE TO RELATED APPLICATIONS

This application claims the benefit of U.S. Provisional Patent Application 61/598,979 filed on Feb. 15, 2012, and entitled CATHETER ASSEMBLY AND METHOD OF TREATING A VASCULAR DISEASE, and of U.S. Provisional Patent Application 61/752,061 filed on Jan. 14, 2013, and entitled CATHETER ASSEMBLY AND METHOD OF TREATING A VASCULAR DISEASE the entirety of which is incorporated by reference herein.

FIELD OF THE INVENTION

The present invention relates to a catheter assembly that comprises a catheter and an elongated hollow needle and to a method of delivering fluid to tissue surrounding a lumen in a body organ with such a catheter assembly and, more particularly, to a catheter assembly in which a needle is movable in a lumen of a catheter to move a distal end of the needle between openings formed in a wall of the catheter and to a method of treating vascular disease with such a catheter assembly.

BACKGROUND OF THE INVENTION

One method for treating varicose veins is endovenous ablation ("EVA"). EVA involves introducing a device for delivering laser or radio frequency energy into a varicose vein to cauterize and close the vein. Implementing EVA generally involves inserting a catheter into the vein to be treated and moving the end of the catheter to the end of the vein. The catheter encloses a device for delivering laser or radio frequency energy. The energy delivery device is activated, and the catheter and the energy delivery device are slowly retracted along the vein. As the catheter and the energy delivery device are retracted, the energy from the energy delivery device destroys the tissue of the vein. The vein collapses and is eventually absorbed by the patient's body.

SUMMARY OF THE INVENTION

The present invention is directed to a catheter assembly that comprises a catheter and an elongated hollow needle and to a method of delivering fluid to tissue surrounding a lumen in a body organ with such a catheter assembly and, more particularly, to a catheter assembly in which a needle is movable in a lumen of a catheter to move a distal end of the needle between openings formed in a wall of the catheter and to a method of treating vascular disease with such a catheter assembly.

In accordance with an embodiment of the present invention, a catheter assembly comprises a catheter. The catheter includes a catheter wall and a lumen extending lengthwise of the catheter wall. The catheter wall has a radially inner surface and a radially outer surface. The catheter wall includes a plurality of openings that extend through the catheter wall from the inner surface to the outer surface. The openings communicate with the lumen. An elongated hollow needle includes a proximal end portion and a distal end portion. The needle is movable in the lumen to move the distal end portion between the openings. The distal end portion is directed radially outward so as to extend into an adjacent one of the openings. The distal end portion has a configuration that stores potential energy when the distal end portion is disposed within the lumen. The potential energy is converted to kinetic energy to produce movement of the proximal end portion as the distal end portion moves from the inner surface of the catheter wall across an edge of the adjacent one of the openings. The movement of the proximal end portion is haptically perceptible.

In accordance with another embodiment of the present invention, a method of delivering fluid to tissue surrounding a lumen in a body organ comprises the step of inserting a catheter assembly into the lumen in the body organ. The catheter assembly includes a catheter and an elongated hollow needle with a proximal end portion and a distal end portion. The catheter includes a catheter wall and a catheter lumen extending lengthwise of the catheter wall. The catheter wall has a radially inner surface and a radially outer surface. The catheter wall includes a plurality of openings that extend through the catheter wall from the inner surface to the outer surface. The openings communicate with the catheter lumen. The distal end portion of the needle is directed radially outward so as to extend into an adjacent one of the openings. The distal end portion of the needle has a configuration to produce movement of the proximal end portion of the needle as the distal end portion moves radially outward from the inner surface of the catheter wall into the adjacent one of the openings. The movement of the proximal end portion is haptically perceptible. The method also comprises the step of moving the needle in the catheter lumen so that the distal end portion of the needle is disposed adjacent an edge of a first one of the plurality of openings. The method further comprises the steps of moving the distal end portion of the needle into the first one of the plurality of openings to produce haptically perceptible movement of the proximal end portion of the needle and extending the distal end portion of the needle into a first portion of tissue outside of the lumen in the body organ. The method still further comprises the steps of introducing a fluid into the first portion of tissue through the hollow needle and retracting the distal end portion of the needle from the first portion of tissue and into the catheter lumen. Yet further, the method comprises the steps of moving the needle in the catheter lumen so that the distal end portion of the needle is disposed adjacent a second one of the plurality of openings, moving the distal end portion of the needle into the second one of the plurality of openings to produce haptically perceptible movement of the proximal end portion of the needle, and extending the distal end portion of the needle into a second portion of tissue outside of the lumen in the body organ. Yet further still, the method comprises the steps of introducing the fluid into the second portion of tissue through the hollow needle, and retracting the distal end portion of the needle from the second portion of tissue and into the catheter lumen.

In accordance with a further embodiment of the present invention, a catheter assembly comprises a catheter. The catheter includes a catheter wall and a lumen extending lengthwise of the catheter wall. The catheter wall has a radially inner surface and a radially outer surface. The catheter wall also includes a plurality of openings that extend through the catheter wall from the inner surface to the outer surface. The openings communicate with the lumen. An elongated hollow needle includes a proximal end portion and a distal end portion. The needle is movable in the lumen to move the distal end portion between the openings. The distal end portion is directed radially outward so as to extend into an adjacent one of the openings. A first part of the distal end portion has a first radius of curvature, and a second part of the distal end portion has a second radius of curvature. The second part of the distal end portion is located distally of the first part of the distal end portion, and the second radius of curvature is smaller than the first radius of curvature.

In accordance with yet another embodiment of the present invention, an elongated hollow needle comprises a proximal end portion, a distal end portion, and a tubular needle wall. The tubular needle wall defines a lumen that extends through the distal end portion to an open distal end of the needle wall. The needle wall is sharpened at its open distal end. The distal end portion of the needle is directed radially outward. A first part of the distal end portion has a first radius of curvature, and a second part of the distal end portion has a second radius of curvature. The second part of the distal end portion is located distally of the first part of the distal end portion, and the second radius of curvature is smaller than the first radius of curvature.

BRIEF DESCRIPTION OF THE DRAWINGS

The foregoing and other features and advantages of the present invention will become apparent to one skilled in the art upon consideration of the following description of the invention and the accompanying drawings, in which:

FIG. 1 is a side view of a catheter assembly in accordance with an embodiment of the present invention;

FIG. 1A is a top view of a first portion of the catheter assembly of FIG. 1;

FIG. 1B is a side view of a second portion of the catheter assembly of FIG. 1;

FIG. 5A is a schematic illustration of certain angles measured with respect to various portions of a needle incorporated in the catheter assembly of FIG. 5;

FIG. 7 is an enlarged sectional view, similar to FIG. 2, of a portion of a catheter assembly in accordance with a fourth embodiment of the present invention; and FIG. 7A is a sectional view taken generally along line 7A-7A of FIG. 7.

DETAILED DESCRIPTION

Figure 2:
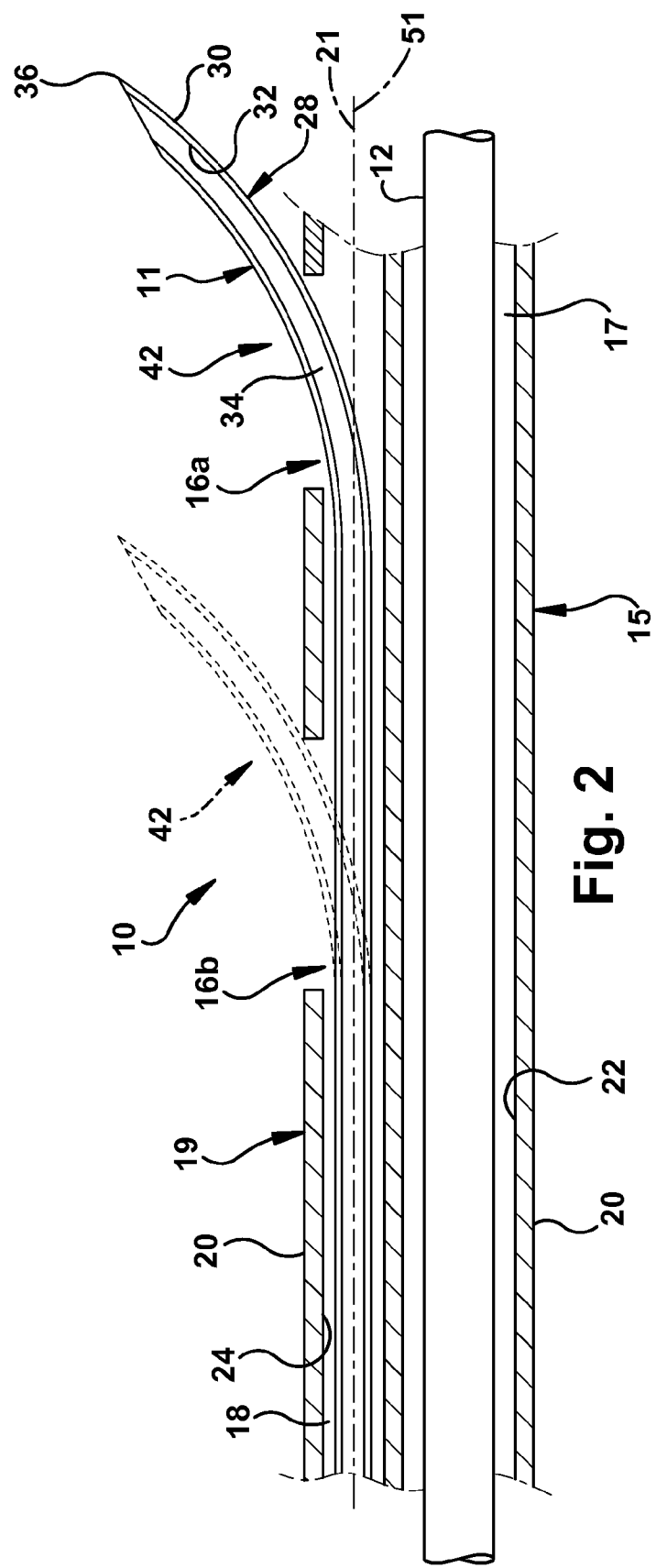
FIG. 2 is an enlarged sectional view of a third portion of the catheter assembly of FIG. 1.

FIGS. 1 through 2 illustrate a catheter assembly 10, in accordance with an example of the present invention. The catheter assembly 10 includes a sheath or catheter 15, which is made of a flexible and resilient bio-compatible material, such as a medical grade elastomer. The catheter 15 includes a catheter wall 19, a first catheter lumen 17 extending lengthwise of the catheter wall, and a second catheter lumen 18 extending lengthwise of the catheter wall.

The catheter wall 19 includes a radially outer surface 20. The catheter wall also includes a first radially inner surface 22 and a second radially inner surface 24. The first radially inner surface 22 at least partially defines the first lumen 17. The second radially inner surface 24 at least partially defines the second lumen 18. The outer surface 20, the first inner surface 22, the second inner surface 24, the first lumen 17, and the second lumen 18 all extend substantially the entire length of the catheter 15 and the catheter wall 19.

The outer surface 20 includes a plurality of ports or openings 16 that extend from the outer surface to the second inner surface 24. The openings 16 communicate with the second lumen 18. As shown in FIG. 1A, the openings 16 are equally spaced apart and are arranged in a straight line or row extending along the length of the catheter 15. If desired, however, the openings 16 could be spaced apart different distances and/or could be offset circumferentially from a straight line. Also, as shown in FIG. 1A, the openings 16 have a generally oval shape. The openings 16 may, however, have other shapes, such as circular, rhomboid (diamond-shaped) or rectangular.

The first lumen 17 is open at both its distal end and its proximal end. The first lumen 17 receives an elongated energy delivery device 12. The energy delivery device 12 is a flexible optical fiber that delivers laser energy. At its proximal end, the energy delivery device 12 is connected to an energy source 26, which is a source of laser energy. The energy delivery device 12 may alternatively be, for example, a metal wire that delivers radio frequency energy. If the energy delivery device 12 delivers radio frequency energy, the energy source 26 is a source of radio frequency energy. As further alternatives, the energy delivery device 12 may constructed to deliver energy in the form of high frequency ultrasound or light other than laser light, and the energy source 26 may be a source of energy in the form of high frequency ultrasound or light other than laser light, respectively.

The second lumen 18 is open at its proximal end and may be open or closed at its distal end. The second lumen 18 has a central longitudinal axis 21 and receives an elongated hollow needle 11. The needle 11 is made of a biocompatible material, such as stainless steel, nitinol or polytetrafluoroethylene ("PTFE"), that has sufficient rigidity to penetrate a patient's tissue and also has sufficient flexibility and resilience to withstand being deflected and then return to a non-deflected position. As shown in FIG. 2, the needle 11 includes a tubular needle wall 28. The needle wall 28 includes a radially outer surface 30 and a radially inner surface 32. The inner surface 32 defines a third lumen 34. A distal tip 36 of the needle 11 is open. The portion of the needle wall 28 at the distal tip 36 is sharpened so that the distal tip of the needle 11 can penetrate tissue of, for example, a vein (not shown) and tissue surrounding the vein. At its proximal end 38, the needle 11 is connected to a reservoir 40 of fluid. The fluid may be a diagnostic fluid, a therapeutic fluid, and/or a fluid to aid in the delivery of energy by, for example, acting as a heat sink. As one example, the fluid may be a tumescent fluid comprising saline solution combined with an anesthetic agent, such as lidocaine. As a result of the construction of the needle, the fluid may flow from the proximal end 38 of the needle 11, through the third lumen 34, and then out of the distal tip 36 of the needle.

At its proximal end 44, the catheter 15 is joined to a Y-connector 13. The Y-connector 13 includes a main body portion 46 and a side arm portion 48. The main body portion 46 includes a first passage (not shown) that communicates with the first lumen 17 in the catheter 15. At the point where the side arm portion 48 of the Y-connector 13 branches off from the main body portion 46, the first passage (not shown) follows the side arm portion. The first passage extends through the side arm portion 48 to the proximal end of the side arm portion. The first passage receives the energy delivery device 12, which extends through the side arm portion 48 of the Y-connector 13 and projects from the proximal end of the side arm portion. A flush port 14 is connected to the side arm portion 48 and communicates with the first passage (not shown) in the side arm portion.

The main body portion 46 of the Y-connector 13 also includes a second passage (not shown) that communicates with the second lumen 18 in the catheter 15. At the point where the side arm portion 48 of the Y-connector 13 branches off from the main body portion 46, the second passage (not shown) follows the main body portion. The second passage extends through the main body portion 46 to the proximal end of the main body portion. The second passage receives the hollow needle 11, which extends through the main body portion 46 of the Y-connector 13 and projects from the proximal end of the main body portion.

The needle 11 includes a distal end portion 42 (FIG. 2) that includes the distal tip 36 of the needle and extends toward the proximal end 38 of the needle for a predetermined distance. The distal end portion 42 has a predetermined hooked or curved configuration. The distal end portion 42 is both sufficiently rigid in a lengthwise direction to permit the needle 11 to penetrate vascular tissue, as well as tissue outside of and surrounding vascular tissue, and sufficiently flexible and resilient in a radial direction to permit the distal end portion to be deflected from its curved configuration and then return to a non-deflected position.

The needle 11 also includes a proximal end portion 50 that includes the proximal end 38 of the needle and extends toward the distal tip 36 of the needle for a predetermined distance. The proximal end portion 50, as well as the remainder of the needle other than the distal end portion 42, is substantially straight as manufactured and has a substantially straight central longitudinal axis 51. When the needle 11 is received in the second lumen 18 and the distal end portion 42 of the needle extends radially outward through an opening 16, as described below, the central longitudinal axis 51 will tend to be coaxial with the central longitudinal axis 21 of the second lumen.

As shown in FIG. 1B, the proximal end portion 50 may optionally include two sets of indicia 52 and 53. The two sets of indicia 52 and 53 are provided to help convey to a user of the catheter assembly 10 information regarding the longitudinal position and rotational position, respectively, of the needle 11. Because the needle 11 has a relatively small outer diameter, the indicia 52 and 53 are formed on a cylindrical plastic ferrule 54 (FIG. 1B) that is secured to the outer surface 30 of the needle wall 28 so as to move with the needle. To provide information about the position of the needle 11 relative to the catheter 15, two additional sets of indicia 56 and 57 are formed on a bracket 58 secured to the Y-connector 13. The bracket 58 may alternatively be secured to any other structure that is secured to the catheter 15 so as to move with the catheter. The bracket 58 is adjacent to, but spaced from the ferrule 54 and the needle 11 so that the needles is free to move longitudinally, laterally, and rotationally relative to the bracket.

The indicia 52 and 56 are hash marks or other markings spaced apart axially along the length of the ferrule 54 and the bracket 58, respectively. The indicia 53 and 57 are hash marks or other markings spaced apart radially around the circumference of the ferrule 54 and the bracket 58, respectively. The indicia 52, 53, 56 and 57 are disposed and formed such that the relative positions of the needle 11 and the catheter 15 may be determined by viewing the relative positions or alignment of the indicia. Although each of the four sets of indicia 52, 53, 56 and 57 is shown as including more than one hash mark, one or more of the sets of indicia may include only a single hash mark or other marking. For example, each of the indicia 52 and 53 may consist of a single hash mark, while each of the indicia 56 and 57 may consist of multiple hash marks. Such an arrangement may allow the indicia 52 and 53 to be formed on or secured directly to the outer surface 30 of the needle wall 28 without the use of the ferrule 54. The ferrule 54 and the bracket 58 may also be components of a handle assembly (not shown) to facilitate manipulation of the needle 11 and/or to lock the needle in position relative to the catheter 15.

In use, the catheter assembly 10 is inserted into a patient's vein (not shown). The needle 11 is received in the second lumen 18 and is movable lengthwise in the second lumen. When the distal end portion 42 of the needle 11 is received in the second lumen 18, the catheter wall 19 deflects the distal end portion of the needle from its curved configuration and constrains the distal end portion in a generally straight configuration. Such deflection and constraint of the distal end portion 42 stores potential energy. As the needle 11 moves lengthwise in the second lumen 18, the distal end portion 42 of the needle moves adjacent successive ones of the openings 16 in the catheter wall 19. When the distal tip 36 of the needle 11 is disposed adjacent an opening 16 in the catheter wall 19, the radial resilience of the distal end portion 42 of the needle directs the distal tip and the distal end portion radially outward. The stored potential energy in the distal end portion 42 is converted to kinetic energy in the moving distal end portion. The distal tip 36 and the distal end portion 42 will then extend radially outward into the adjacent opening 16.

If the distal tip 36 of the needle 11 is initially positioned at the distal end of the second lumen 18, the needle may be withdrawn or moved lengthwise through the second lumen toward the proximal end 44 of the catheter 15. By orienting the needle 11 appropriately about its longitudinal axis, the distal tip 36 can be positioned so as to be directed into successive ones of the openings 16 in the catheter wall 19. Specifically, as the distal tip 36 approaches the opening 16a (FIG. 2) closest to the distal end of the second lumen 18, the distal tip will move along the second inner surface 24 of the catheter wall 19. When the distal tip 36 moves to a position directly adjacent to the opening 16a, the distal tip will be directed into the opening and away from the longitudinal axis 21 of the second lumen 18 by the resilient bias of the distal end portion 42 of the needle 11.

The resilient radial bias of the distal end portion 42 of the needle 11 will also produce a movement of the needle that will be haptically perceptible to the user of the catheter assembly 10. More particularly, the distal end portion 42 is configured to produce haptically perceptible movement of the proximal end portion 50 of the needle 11 in response to radially outward movement of the distal end portion. Consequently, when the user of the catheter assembly detects a movement or vibration of the needle 11 indicating that the distal tip 36 has been extended into the opening 16a, the user can then reverse the longitudinal movement of the needle. Such reverse movement will cause the distal end portion 42 of the needle 11 to extend into and through the opening 16a to a greater distance or extent so as to penetrate the adjacent tissue of the patient. The adjacent tissue will include both the tissue of the patient's vein and tissue surrounding the patient's vein. When the distal end portion 42 has penetrated the adjacent tissue of the patient to a sufficient distance or extent, fluid may be introduced into the tissue through the needle 11. The fluid may, for example, be a tumescent fluid comprising saline solution combined with an anesthetic agent, such as lidocaine.

After a predetermined amount of fluid has been introduced into the tissue adjacent the opening 16a closest to the distal end of the second lumen 18, the user of the catheter assembly 10 can resume moving the needle 11 lengthwise through the second lumen 18 toward the proximal end 44 of the catheter 15. The resumed movement toward the proximal end 44 of the catheter 15 retracts or withdraws the distal end portion 42 of the needle 11 into the second lumen 18 from the tissue adjacent the opening 16a closest to the distal end of the second lumen 18. The catheter wall 19 again deflects the distal end portion 42 of the needle 11 from its curved configuration and toward the longitudinal axis 21 of the second lumen 18, and the distal tip 36 of the needle moves along the second inner surface 24 of the catheter wall. As the distal tip 36 of the needle 11 moves to a position directly adjacent to an opening 16b (FIG. 2) that is next closest to the distal end of the second lumen 18, the distal tip will be directed into the opening 16b and away from the longitudinal axis 21 of the second lumen 18 by the resilient bias of the distal end portion 42 of the needle 11.

The resilient radial bias of the distal end portion 42 of the needle 11 will also produce a movement of the needle that will be haptically perceptible to the user of the catheter assembly 10. As previously described, the distal end portion 42 is configured to produce haptically perceptible movement of a proximal end portion 50 of the needle 11 in response to radially outward movement of the distal end portion. Consequently, when the user of the catheter assembly detects a movement or vibration of the needle 11 indicating that the distal tip 36 has been extended into the opening 16b, the user can then reverse the longitudinal movement of the needle. Such reverse movement will cause the distal end portion 42 of the needle 11 to extend into and through the opening 16b to a greater distance or extent so as to penetrate the adjacent tissue of the patient. The adjacent tissue will include both the tissue of the patient's vein and tissue surrounding the patient's vein. When the distal end portion 42 has penetrated the adjacent tissue of the patient to a sufficient distance or extent, fluid may be introduced into the tissue through the needle 11.

After a predetermined amount of fluid has been introduced into the tissue adjacent the opening 16b, the user of the catheter assembly 10 can resume moving the needle 11 lengthwise through the second lumen 18 toward the proximal end 44 of the catheter 15. The resumed movement toward the proximal end 44 of the catheter 15 retracts or withdraws the distal end portion 42 of the needle 11 into the second lumen 18 from the tissue adjacent the opening 16b. The catheter wall 19 again deflects the distal end portion 42 of the needle 11 from its curved configuration and toward the longitudinal axis 21 of the second lumen 18, and the distal tip 36 of the needle moves along the second inner surface 24 of the catheter wall.

The user of the catheter assembly 10 can repeat the above described movements as the needle 11 is moved lengthwise through the second lumen 18 toward the proximal end 44 of the catheter 15 and the distal end portion 42 of the needle is correspondingly moved to positions directly adjacent to successive openings 16 that are increasingly farther from the distal end of the second lumen 18. The above described movements may be repeated as many times as may be desired or required to introduce fluid into a length of vascular and/or other tissue that is selected by the user of the catheter assembly 10 either before or after introducing the catheter assembly into the patient's vein.

In addition, if the user of the catheter assembly 10 determines that it is necessary or desirable to return to a portion of tissue located distally of the distal tip 36 of the needle 11 to introduce additional fluid, the needle may be conveniently moved in a distal direction by first rotating the needle away from the openings 16 and then moving the needle in a distal direction. When the distal tip 36 of the needle 11 is positioned axially or lengthwise adjacent the selected portion of tissue into which additional fluid is to be introduced, the needle can be rotated back into alignment with the openings 16 to extend through a selected opening into the selected portion of tissue. The indicia 52, 53, 56 and 57 can facilitate such rotational movement of the needle 11 away from the openings 16, distal movement of the needle 11 to the desired position lengthwise in the catheter 15, and subsequent rotation of the needle back into to alignment with the openings.

After fluid has been introduced into a desired length of vascular and/or other tissue adjacent the catheter assembly 10, the distal end of the energy delivery device 12 is moved to a position at or beyond the distal end of the catheter 15 and the first lumen 17, if the energy delivery device is not already in such a position. Laser (or, alternatively, radio frequency, high frequency ultrasound, or light other than laser light) energy is then delivered by the energy delivery device 12 to the tissue adjacent to the distal end of the energy delivery device. The catheter 15 and the energy delivery device 12 are slowly retracted together along the vein. As the catheter 15 and the energy delivery device 12 are retracted, the energy from the energy delivery device destroys the tissue of the vein. During the foregoing treatment process, the fluid that has previously been injected into the patient's tissue acts as a heat sink so that tissue around the vein tends not to be affected by heat produced by the delivery of energy via the energy delivery device 12. The fluid also constricts the vein from outside the vein so that treatment of the vein tends to be more effective, and anesthetic in the fluid helps numb any sensation of pain. As a result of the treatment process, the vein collapses and is eventually absorbed by the patient's body.

Figure 3:
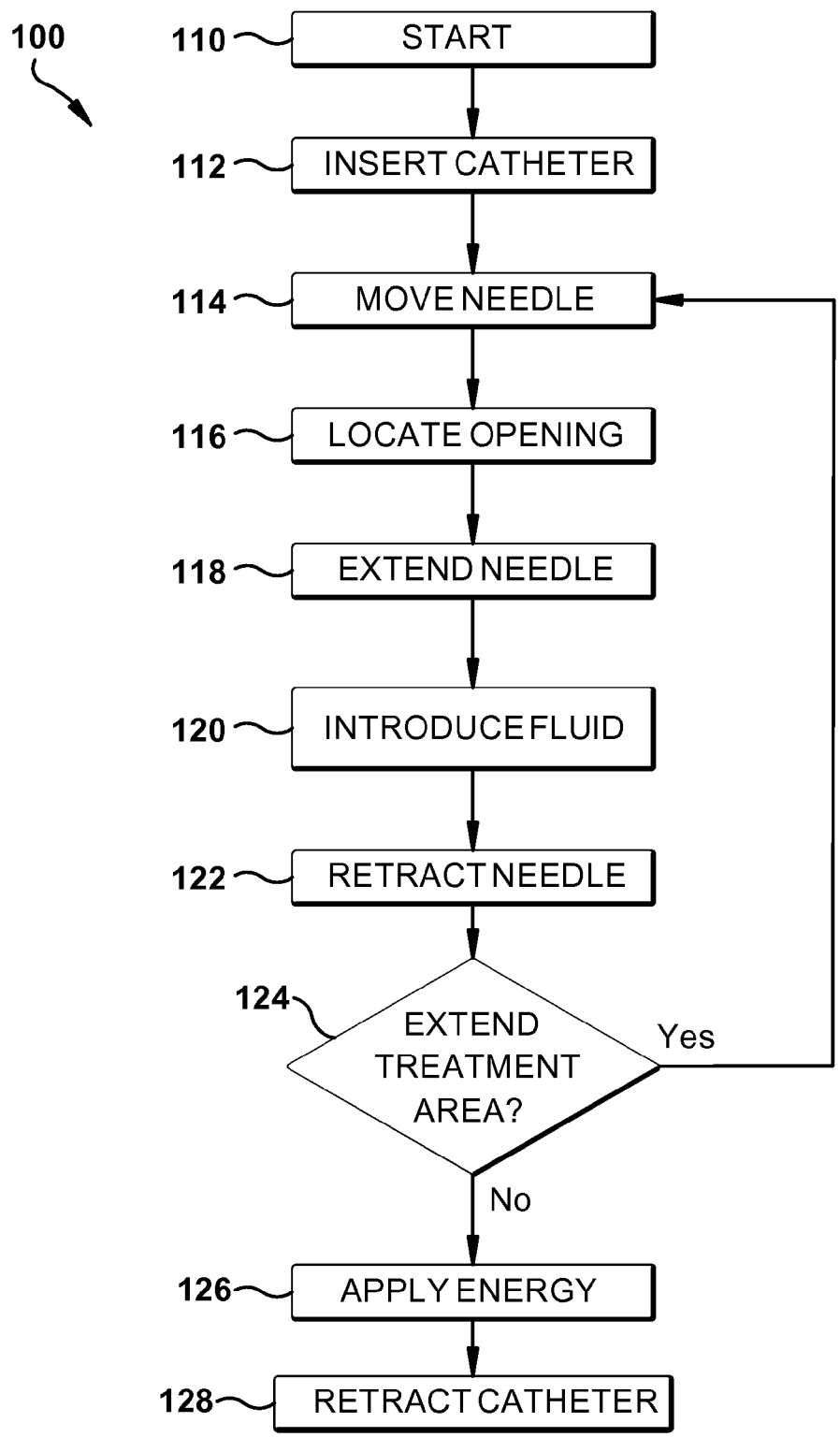
FIG. 3 is a flow chart showing steps in a method for treating vascular disease using the catheter assembly of FIG. 1 in accordance with an embodiment of the present invention.

As shown in FIG. 3, an embodiment of a process 100 for a method of treating vascular disease, such as varicose veins, with a catheter assembly such as shown in FIGS. 1-2 begins at step 110. The process 100 then proceeds to step 112 in which a catheter assembly, such as the catheter assembly 10 shown in FIGS. 1-2, is inserted into a patient's vessel. The process 100 next proceeds to step 114 in which a hollow needle, such as the needle 11 of FIGS. 1-2, is moved along a lumen of a catheter included in the catheter assembly. The process 100 further proceeds to step 116 in which a first one of a plurality of openings in a radially outer surface of the catheter is located via a haptically perceptible movement of a proximal end portion of the needle in response to radially outward movement of the distal end portion as the needle moves to a position directly adjacent the opening and a distal tip of the needle is directed into the opening. The process 100 thereafter proceeds to step 118 in which the distal end portion of the needle is extended into the first one of the plurality of openings, through the tissue of the vessel, and into a first portion of tissue outside of the vessel. In step 120, a fluid is introduced into the first portion of tissue through the needle. The distal end portion of the needle, in step 122, is then retracted from the first portion of tissue and into the lumen of the catheter.

At step 124 of the process 100, a determination is made as to whether a sufficient area or lengthwise portion of the patient's vein has been treated with fluid and, therefore, whether the treatment area or lengthwise portion should be extended. If the determination as to extending the treatment area is positive, the process 100 returns to step 114 and the needle is moved along the lumen of a catheter toward a second one of the plurality of openings in the radially outer surface of the needle. The process further proceeds to step 116 in which the second one of the plurality of openings in the radially outer surface of the catheter is located via a haptically perceptible movement of a proximal end portion of the needle in response to radially outward movement of the distal end portion as the needle moves to a position directly adjacent the opening and the distal tip of the needle is directed into the opening. The process 100 thereafter proceeds to step 118 in which the distal end portion of the needle is extended into the second one of the plurality of openings, through the tissue of the vessel, and into a second portion of tissue outside of the vessel. In step 120, the fluid is introduced into the second portion of tissue through the needle. The distal end portion of the needle, in step 122, is then retracted from the second portion of tissue and into the lumen of the catheter.

At step 124 of the process 100, a determination is again made as to whether a sufficient area or lengthwise portion of the patient's vein has been treated with tumescent fluid and, therefore, whether the treatment area or lengthwise portion should be extended. If the determination as to extending the treatment area is now negative, the process 100 moves on to step 126 in which laser (or, alternatively, radio frequency, high frequency ultrasound, or light other than laser light) energy is delivered by an energy delivery device, such as the energy delivery device 12 of FIGS. 1-2, to the tissue adjacent to the distal end of the energy delivery device. In step 128, the catheter and the energy delivery device are slowly retracted along the vein. As the catheter and the energy delivery device are retracted, the energy from the energy delivery device destroys the tissue of the vein.

Figure 4:
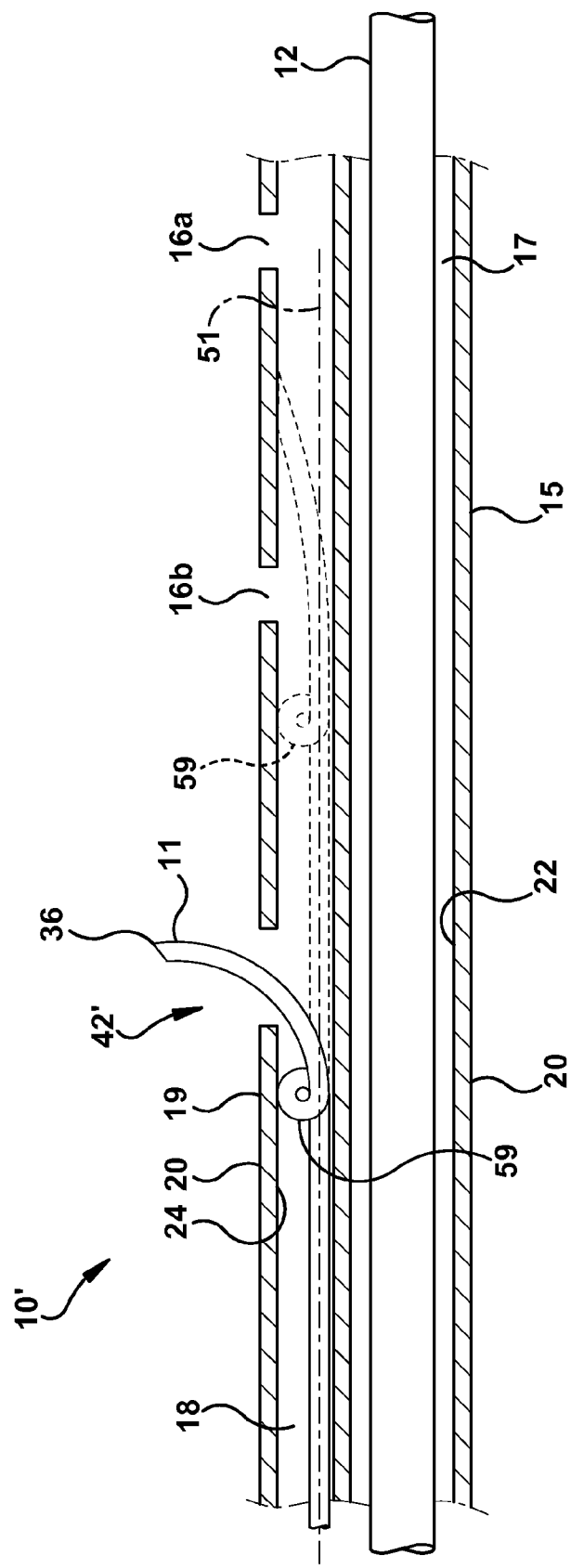
FIG. 4 is an enlarged sectional view, similar to FIG. 2, of a portion of a catheter assembly in accordance with a second embodiment of the present invention.

Although the distal end portion 42 of the needle 11 is shown in FIGS. 1-2 as having a predetermined smoothly curved configuration and as projecting radially outwardly, the distal end portion may have other predetermined configurations. For example, FIG. 4 shows a catheter assembly 10' in accordance with a second embodiment of the present invention, in which the distal end portion 42' of the needle 11 includes a coil 59 that is axially spaced from the distal tip 36 of the needle. The coil 59 acts as a spring to increase the radial bias or resilience in a radial direction of the distal end portion 42' of the needle 11 and thereby increase the force with which the distal end portion can penetrate vascular tissue, as well as tissue outside of and surrounding vascular tissue. The distal end portion 42 of the needle 11 may have still other predetermined configurations, such as an angled configuration, and may project from the catheter 15 in other directions, such as ninety degrees or another angle from the catheter and from the central longitudinal axis 51 or axially through the distal end of the catheter. Also, while the method of treating vascular disease as described above involves positioning a hollow needle, such as the needle 11 of FIGS. 1-2, so that its distal end portion is adjacent the distal end of a catheter and moving the needle toward the proximal end of the catheter, the method could also be implemented by positioning the needle so that its distal end portion is near the proximal end of the catheter and moving the needle toward the distal end of the catheter.

Figure 5:
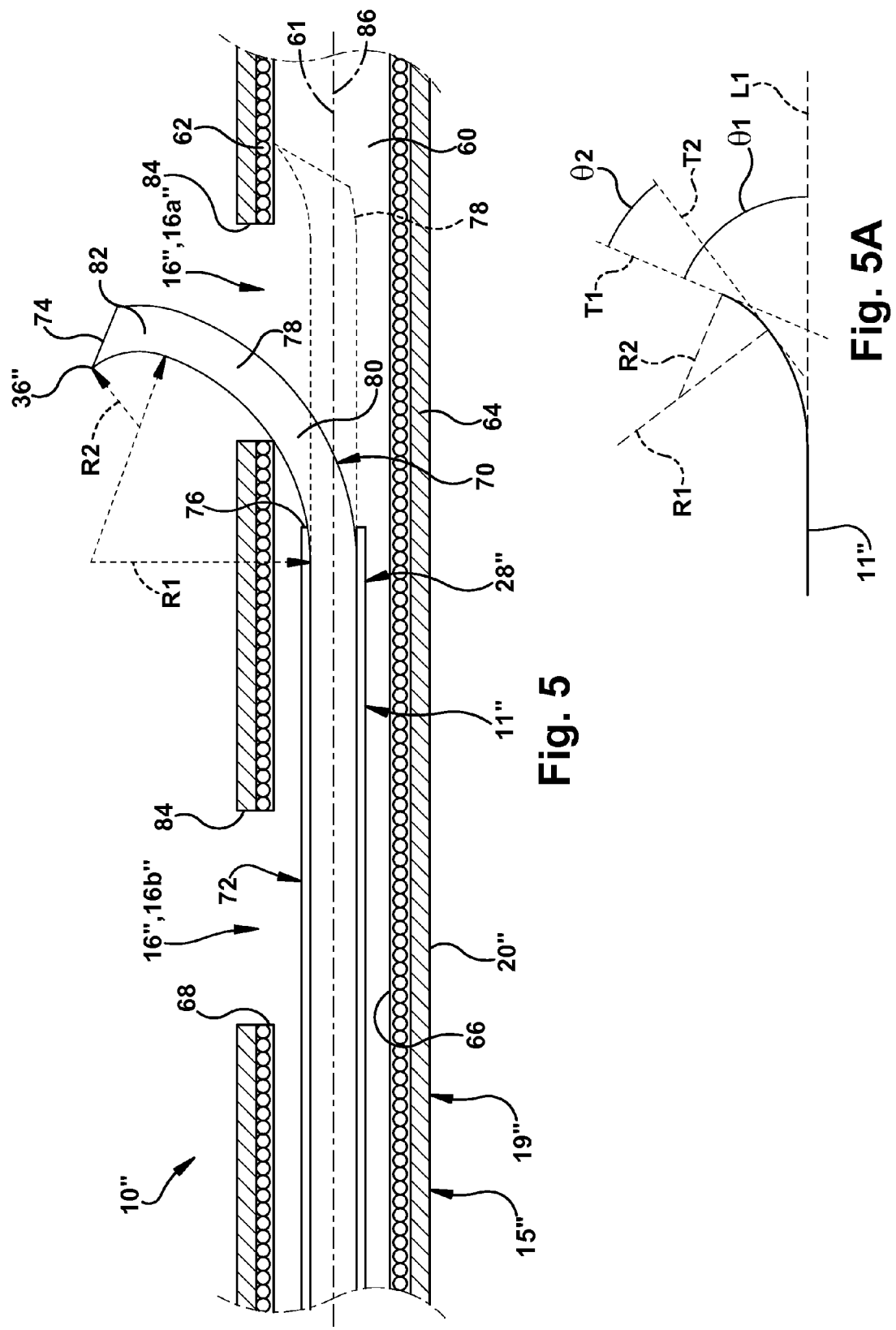
FIG. 5 is an enlarged sectional view, similar to FIG. 2, of a portion of a catheter assembly in accordance with a third embodiment of the present invention.

As a further alternative, one of the first and second lumens 17 and 18 of the catheter 15 shown in FIGS. 1-2 could be eliminated. FIG. 5 illustrates a catheter assembly 10", in accordance with a third embodiment of the present invention. The catheter assembly 10" is similar in construction to the catheter assembly 10 but the catheter 15" of the catheter assembly 10" includes only a single catheter lumen. More particularly, the sheath or catheter 15" includes a catheter wall 19" and a single catheter lumen 60 extending lengthwise of the catheter wall. The catheter wall 19" is made of two coaxial layers of different materials. The radially inner layer 62 is formed of coiled or braided strands of a bio-compatible metallic or polymeric material. The radially outer layer 64 is formed of a homogeneous mass of a flexible bio-compatible material, such as a medical grade polymer or a medical grade elastomer.

The inner layer 62 of the catheter wall 19" provides additional column strength to the catheter wall and inhibits kinking of the catheter 15". The inner layer 62 also inhibits piercing of the catheter wall 19" by, for example, a needle. Although the inner layer 62 is shown as being formed of coiled or braided strands of material, the inner layer may be formed of other types and/or configurations of reinforcing material. If the inner layer 62 is formed of a metallic material, the catheter 15" will tend to be more readily and clearly detected by ultrasound. Further, the inner layer 62 may be formed of a material that is similar to, but less flexible than (e.g., higher durometer) than the material used in the outer layer 64 or may be eliminated entirely. If the inner layer 62 is formed of a softer material or eliminated, however, the catheter 15" will tend to be more easily pierced.

The catheter wall 19" includes a radially outer surface 20" and a radially inner surface 66. The outer surface 20" is provided by a radially outer surface of the outer layer 64 of the catheter wall 19". The inner surface 66 is provided by a radially inner surface of the inner layer 62 of the catheter wall 19". The inner surface 66 at least partially defines the single lumen 60. A coating 68 formed of a hydrophilic material may optionally be applied to the inner surface 66, as shown, and/or to the outer surface 20" (not shown). The outer surface 20", the inner surface 66, and the lumen 60 all extend substantially the entire length of the catheter 15" and the catheter wall 19".

The outer surface 20" includes a plurality of ports or openings 16" that extend from the outer surface to the inner surface 66. The openings 16" communicate with the lumen 60 and may have a variety of shapes and sizes. The openings 16" may, for example, be circular in shape and have a diameter in a range from about 1.5 mm to about 3.0 mm. The openings 16" may, however, have other shapes, such as oval, rhomboid (diamond-shaped) or rectangular. Although the openings 16" are shown in FIG. 5 as being defined by circumferential surfaces 84 that extend substantially perpendicular to the inner surface 66 and the outer surface 20" of the catheter wall 19", the openings may be defined by circumferential surfaces that extend at another angle to the inner and outer surfaces of the catheter wall or that are curved. If the circumferential surfaces 84 of the catheter wall 19" extend at an angle to or are curved relative to the inner surface 66 and the outer surface 20", the circumferential surfaces can provide ramps for a needle to move into or out of the lumen 60.

Because the catheter wall 19" includes an inner layer 62 that provides reinforcement for the catheter wall and inhibits kinking of the catheter 15", the openings 16" tend to diminish the functioning of the inner layer in this regard. It may be desirable, therefore, to provide a ring of reinforcement material (not shown) that either surrounds the circumferential surface 84 defining each opening 16" or provides the circumferential surface for each opening, in order to help inhibit kinking of the catheter 15". Like the openings 16 in the catheter wall 19 shown in FIG. 1A, the openings 16" may be equally spaced apart and arranged in a straight line or row extending along the length of the catheter 15". If desired, however, the openings 16" could be spaced apart different distances and/or could be offset circumferentially from a straight line.

Like the first and second lumens 17 and 18 of FIGS. 1-2, the lumen 60 is open at both its distal end and its proximal end. The lumen 60 has a central longitudinal axis 61 and receives, at different times, an elongated energy delivery device, such as the energy delivery device 12, and an elongated hollow needle 11". The needle 11" is made of the same materials as the needle 11 of FIGS. 1-2 and has generally the same construction as the needle 11 of FIGS. 1-2. Unlike the needle 11, however, the needle 11" has a tubular needle wall 28" with two different thicknesses.

As shown in FIG. 5, the needle wall 28" is formed of coaxial inner and outer hypotubes 70 and 72. The radially outer hypotube 72 has a larger outer diameter and a larger inner diameter than the radially inner hypotube 70. For example, the outer hypotube 72 may have an outer diameter of about 1.6 mm, and the inner hypotube 70 may have an outer diameter of about 1.2 mm. The outer hypotube 72 receives the inner hypotube 70 and is secured to the inner hypotube to inhibit relative longitudinal movement of the inner and outer hypotubes. The outer diameters of the inner and outer hypotubes 70 and 72 and the sizes of the openings 16" are selected such that the inner hypotube can pass through the openings, but the outer hypotube cannot pass through the openings. In this regard, the sizes of the openings 16" in FIG. 5 have been exaggerated for clarity of illustration and do not reflect the actual relationship of the opening sizes to the outer diameters of the inner and outer hypotubes 70 and 72.

Although the needle wall 28" as shown is formed of two hypotubes 70 and 72 having different outer diameters, the needle wall could alternatively be formed of a single hypotube with two different outer diameters or of a single hypotube with a single outer diameter. If the needle wall 28" is formed of a single hypotube with a single outer diameter, the hypotube will be able to pass through the openings 16" without restriction, as there will be no interference between a larger diameter hypotube or a larger diameter portion of a single hypotube and the circumferential surfaces 84 of the catheter wall 19" that define the openings.

The inner hypotube 70 of the needle wall 28" has a distal end 74 that is disposed a predetermined distance beyond the distal end 76 of the outer hypotube 72. As a result, the inner hypotube 70 and, thus, the needle 11" has a distal end portion 78 that extends beyond the outer hypotube 72. The distal end portion 78 make extend proximally just to the distal end 76 of the outer hypotube 72 or to a location that is proximal of the distal end of the outer hypotube. The distal end portion 78 of the inner hypotube 70 and the needle 11" is formed with two different configurations. Specifically, the distal end portion 78 of the inner hypotube 70 and the needle 11" is curved and has two different radii of curvature R1 and R2. For example, the radius of curvature R1 may be in a range from about 2.5 cm to about 10 cm, and the radius of curvature R2 may be in a range from about 0.5 cm to about 5 cm. A proximal part 80 of the distal end portion 78 adjacent the distal end 76 of the outer hypotube 72 is formed with a first configuration and has the relatively larger radius of curvature R1. A distal part 82 of the distal end portion 78 adjacent the distal end 74 of the inner hypotube 70 is formed with a second configuration and has the relatively smaller radius of curvature R2. The distal part 82 of the distal end portion 78 may have a length in a range from about 1 mm to about 2 mm. The proximal part 80 of the distal end portion 78 has a length that is greater than the length of the distal part 82 of the distal end portion. Together, the distal part 82 of the distal end portion 78 and the proximal part 80 of the distal end portion may have a minimum combined length in the range of about 1.5 cm to about 2.0 cm.

The distal end 74 of the inner hypotube 70 is open and sharpened and provides the distal tip 36" of the needle 11". The distal end portion 78 of the inner hypotube 70 and the needle 11" is both sufficiently rigid in a lengthwise direction to permit the needle 11" to penetrate vascular tissue, as well as tissue outside of and surrounding vascular tissue, and sufficiently flexible and resilient in a radial direction to permit the distal end portion to be deflected from its curved configuration and then return to a non-deflected position.

The needle 11" also includes a proximal end portion (not shown) that includes the proximal end (not shown) of the needle and extends toward the distal tip 36" of the needle for a predetermined distance. The proximal end portion of the needle 11" may be similar in construction to the proximal end portion 50 of the needle 11 of FIGS. 1-2. The proximal end portion, as well as the remainder of the needle 11" other than the distal end portion 78 (i.e., the major portion of the needle), is substantially straight as manufactured and has a substantially straight central longitudinal axis 86. When the needle 11" is received in the lumen 60 and the distal end portion 78 of the needle extends radially outward through an opening 16", as described below, the central longitudinal axis 86 will tend to be coaxial with the central longitudinal axis 61 of the lumen.

Like the proximal end portion 50 of the needle 11 of FIGS. 1-2, the proximal end portion (not shown) of the needle 11" may include indicia similar to the indicia 52 and 53 of FIG. 5B. These indicia, like the indicia 52 and 53, may be formed on a plastic ferrule (not shown) that is secured to the outer surface of the needle wall so as to move with the needle 11". To provide information about the position of the needle 11" relative to the catheter 15", two additional sets of indicia (not shown), like the indicia 56 and 57, may be formed on a bracket secured to a structure that, in turn, is secured to the catheter 15" so as to move with the catheter.

In use, the catheter assembly 10" is inserted into a patient's vein (not shown). The needle 11" is received in the lumen 60 and is movable lengthwise in the lumen. When the distal end portion 78 of the inner hypotube 70 of the needle 11" is received in the lumen 60, the catheter wall 19" deflects the distal end portion of the inner hypotube from its curved configuration and constrains the distal end portion in a generally straight configuration (shown in dashed lines in FIG. 5). Such deflection and constraint of the distal end portion 78 stores potential energy. As the needle 11" moves lengthwise in the lumen 60 and the distal end portion 78 of the inner hypotube 70 moves along the radially inner surface 66 of the catheter wall 19", the distal end portion 78 of the inner hypotube 70 moves adjacent successive ones of the openings 16" in the catheter wall 19". When the distal tip 36" of the needle 11" is disposed adjacent an opening 16" in the catheter wall 19", the radial resilience of the distal end portion 78 of the inner hypotube 70 directs the distal tip and the distal end portion radially outward. The stored potential energy in the distal end portion 78 is converted to kinetic energy in the moving distal end portion.

More particularly, as the distal tip 36" of the needle 11" and the distal end portion 78 approach a circumferential edge of an opening 16", at which the circumferential surface 84 of the catheter wall 19" meets or intersects the inner surface 66, the inner surface of the catheter wall constrains radial movement of the needle. Such constraint of the distal end portion 78 maintains the stored potential energy of the deflected distal end portion. When the distal tip 36" of the needle 11" and the distal end portion 78 moves across the circumferential edge of the opening 16" and into the opening, the inner surface 66 of the catheter wall 19" no longer constrains radial movement of the needle. The radial resilience of the distal end portion 78 of the inner hypotube 70 then directs the distal tip 36" and the distal end portion radially outward and away from the longitudinal axis 61 of the lumen 60 and the longitudinal axis 86 of the major portion of the needle 11". As a result, the distal tip 36" and the distal end portion 78 will extend radially outward into the adjacent opening 16". The stored potential energy in the distal end portion 78 is converted to kinetic energy in the moving distal end portion.

When the needle 11" flexes from a generally straight configuration constrained by the catheter wall 19" into a less constrained or unconstrained curved configuration and extends radially outward into an adjacent opening 16", the movement of the distal end portion 78 of the needle 11" will be haptically perceptible to a user of the catheter assembly 10". More particularly, the distal end portion 78 is configured to produce haptically perceptible movement of the proximal end portion (not shown in FIG. 5) of the needle 11" in response to radially outward movement of the distal end portion. Consequently, when the user of the catheter assembly detects a movement or vibration of the needle 11" indicating that the distal tip 36" has been extended into an opening 16", the user can then reverse the longitudinal movement of the needle. Such reverse movement will cause the distal end portion 78 of the needle 11" to extend into and through the adjacent opening 16" to a greater distance or extent so as to penetrate the adjacent tissue of the patient. The adjacent tissue will include both the tissue of the patient's vein and tissue surrounding the patient's vein. When the distal end portion 78 has penetrated the adjacent tissue of the patient to a sufficient distance or extent, fluid may be introduced into the tissue through the needle 11". The fluid may, for example, be a tumescent fluid comprising saline solution combined with an anesthetic agent, such as lidocaine.

After a predetermined amount of fluid has been introduced into the tissue adjacent the opening 16", the user of the catheter assembly 10" can move the needle to another opening. For example, if the distal tip 36" of the needle 11" is initially positioned at the distal end of the lumen 60, the distal tip 36" is initially extended into the opening 16a" closest to the distal end (not shown) of the lumen 60. When the user of the catheter assembly 10" resumes moving the needle 11", such movement will be lengthwise through the lumen 60 toward the proximal end (not shown) of the catheter 15". The resumed movement toward the proximal end of the catheter 15" retracts or withdraws the distal end portion 78 of the needle 11 into the lumen 60 from the tissue adjacent the opening 16a" closest to the distal end of the lumen. The catheter wall 19" again deflects the distal end portion 78 of the needle 11" from its curved configuration and toward the longitudinal axis 61 of the lumen 60 and the longitudinal axis 86 of the major portion of the needle 11", which stores potential energy in the distal end portion. The distal tip 36" of the needle moves along the inner surface 66 of the catheter wall. As the distal tip 36" of the needle 11" moves to a position directly adjacent to an opening 16b" that is next closest to the distal end of the lumen 60, the distal tip will be directed into the opening 16b" and away from the longitudinal axis 61 of the lumen 60 and the longitudinal axis 86 of the major portion of the needle 11" by the resilient bias of the distal end portion 78 of the needle. The stored potential energy in the distal end portion 78 is converted to kinetic energy in the moving distal end portion.

The resilient radial bias of the distal end portion 78 of the needle 11" will also produce a movement of the needle that will be haptically perceptible to the user of the catheter assembly 10". As previously described, the distal end portion 78 is configured to produce haptically perceptible movement of a proximal end portion (not shown) of the needle 11" in response to conversion of stored potential energy in the distal end portion to kinetic energy, as manifested in radially outward movement of the distal end portion. Consequently, when the user of the catheter assembly detects a movement or vibration of the needle 11" indicating that the distal tip 36" has been extended into the opening 16b", the user can then reverse the longitudinal movement of the needle. Such reverse movement will cause the distal end portion 78 of the needle 11" to extend into and through the opening 16b" to a greater distance or extent so as to penetrate the adjacent tissue of the patient. The adjacent tissue will include both the tissue of the patient's vein and tissue surrounding the patient's vein. When the distal end portion 78 has penetrated the adjacent tissue of the patient to a sufficient distance or extent, fluid may be introduced into the tissue through the needle 11".

After a predetermined amount of fluid has been introduced into the tissue adjacent the opening 16b", the user of the catheter assembly 10" can resume moving the needle 11" lengthwise through the lumen 60 toward the proximal end of the catheter 15". The resumed movement toward the proximal end of the catheter 15" retracts or withdraws the distal end portion 78 of the needle 11" into the lumen 60 from the tissue adjacent the opening 16b". The catheter wall 19" again deflects the distal end portion 78 of the needle 11" from its curved configuration and toward the longitudinal axis 61 of the lumen 60 and the longitudinal axis 86 of the major portion of the needle 11", and the distal tip 36" of the needle moves along the inner surface 66 of the catheter wall.

The user of the catheter assembly 10" can repeat the above described movements as the needle 11" is moved lengthwise through the lumen 60 toward the proximal end of the catheter 15" and the distal end portion 78 of the needle is correspondingly moved to positions directly adjacent to successive openings 16" that are increasingly farther from the distal end of the lumen 60. The above described movements may be repeated as many times as may be desired or required to introduce fluid into a length of vascular and/or other tissue that is selected by the user of the catheter assembly 10" either before or after introducing the catheter assembly into the patient's vein.

In addition, if the user of the catheter assembly 10" determines that it is necessary or desirable to return to a portion of tissue located distally of the distal tip 36" of the needle 11" to introduce additional fluid, the needle may be conveniently moved in a distal direction by first rotating the needle away from the openings 16" and then moving the needle in a distal direction. When the distal tip 36" of the needle 11" is positioned axially or lengthwise adjacent the selected portion of tissue into which additional fluid is to be introduced, the needle can be rotated back into alignment with the openings 16" to extend through a selected opening into the selected portion of tissue. The optional indicia can facilitate such rotational movement of the needle 11" away from the openings 16", distal movement of the needle 11" to the desired position lengthwise in the catheter 15", and subsequent rotation of the needle back into to alignment with the openings.

After fluid has been introduced into a desired length of vascular and/or other tissue adjacent the catheter assembly 10", the user of the catheter assembly can remove the needle 11" from the catheter assembly and introduce an energy delivery device, such as the energy delivery device 12 of FIGS. 1-2, into the lumen 60 of the catheter assembly. The distal end of the energy delivery device 12 is moved to a position at or beyond the distal end of the catheter 15" and the lumen 60. Laser (or, alternatively, radio frequency, high frequency ultrasound, or light other than laser light) energy is then delivered by the energy delivery device 12 to the tissue adjacent to the distal end of the energy delivery device. The catheter 15" and the energy delivery device 12 are slowly retracted together along the vein. As the catheter 15" and the energy delivery device 12 are retracted, the energy from the energy delivery device destroys the tissue of the vein. During the foregoing treatment process, the fluid that has previously been injected into the patient's tissue acts as a heat sink so that tissue around the vein tends not to be affected by heat produced by the delivery of energy via the energy delivery device 12. The fluid also constricts the vein from outside the vein so that treatment of the vein tends to be more effective, and anesthetic in the fluid helps numb any sensation of pain. As a result of the treatment process, the vein collapses and is eventually absorbed by the patient's body.

Figure 6:
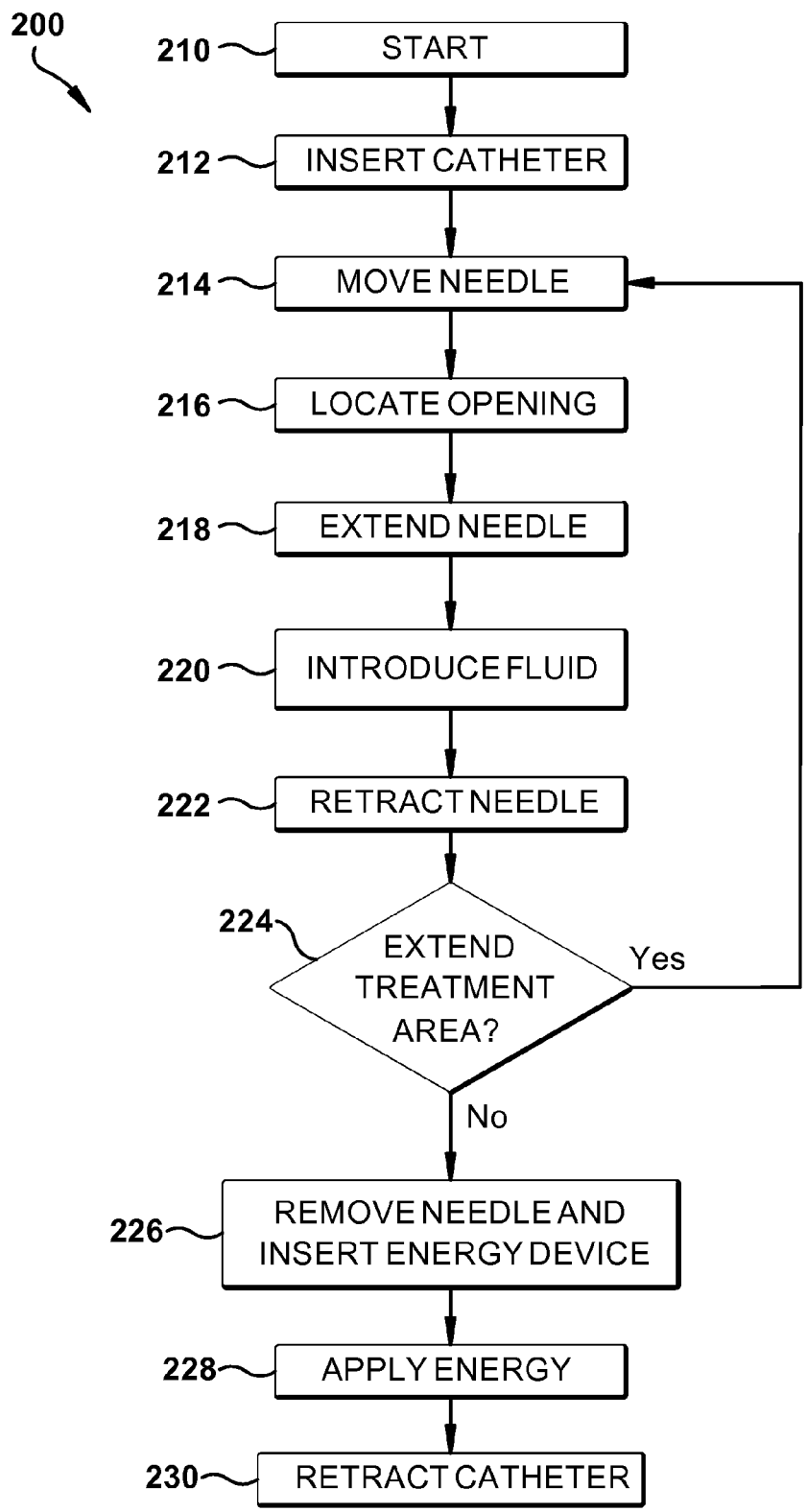
FIG. 6 is a flow chart showing steps in a method for treating vascular disease using the catheter assembly of FIG. 5 in accordance with an embodiment of the present invention.

As shown in FIG. 6, an embodiment of a process 200 for a method of treating vascular disease, such as varicose veins, with a catheter assembly such as shown in FIG. 5 begins at step 210. The process 200 then proceeds to step 212 in which a catheter assembly, such as the catheter assembly 10" shown in FIG. 5, is inserted into a patient's vessel. The process 200 next proceeds to step 214 in which a hollow needle, such as the needle 11" of FIG. 5, is moved along a lumen of a catheter included in the catheter assembly. The process 200 further proceeds to step 216 in which a first one of a plurality of openings in a radially outer surface of the catheter is located via a haptically perceptible movement of a proximal end portion of the needle in response to radially outward movement of the distal end portion as the needle moves to a position directly adjacent the opening and a distal tip of the needle is directed into the opening. The process 200 thereafter proceeds to step 218 in which the distal end portion of the needle is extended into the first one of the plurality of openings, through the tissue of the vessel, and into a first portion of tissue outside of the vessel. In step 220, a fluid is introduced into the first portion of tissue through the needle. The distal end portion of the needle, in step 222, is then retracted from the first portion of tissue and into the lumen of the catheter.

At step 224 of the process 200, a determination is made as to whether a sufficient area or lengthwise portion of the patient's vein has been treated with fluid and, therefore, whether the treatment area or lengthwise portion should be extended. If the determination as to extending the treatment area is positive, the process 200 returns to step 214 and the needle is moved along the lumen of a catheter toward a second one of the plurality of openings in the radially outer surface of the needle. The process further proceeds to step 216 in which the second one of the plurality of openings in the radially outer surface of the catheter is located via a haptically perceptible movement of a proximal end portion of the needle in response to radially outward movement of the distal end portion as the needle moves to a position directly adjacent the opening and the distal tip of the needle is directed into the opening. The process 200 thereafter proceeds to step 218 in which the distal end portion of the needle is extended into the second one of the plurality of openings, through the tissue of the vessel, and into a second portion of tissue outside of the vessel. In step 220, the fluid is introduced into the second portion of tissue through the needle. The distal end portion of the needle, in step 222, is then retracted from the second portion of tissue and into the lumen of the catheter.

At step 224 of the process 200, a determination is again made as to whether a sufficient area or lengthwise portion of the patient's vein has been treated with tumescent fluid and, therefore, whether the treatment area or lengthwise portion should be extended. If the determination as to extending the treatment area is now negative, the process 200 moves on to step 226 in which the needle 11" is removed from the catheter assembly and an energy delivery device, such as the energy delivery device 12 of FIGS. 1-2, is inserted into the central lumen of the catheter. In step 228 of the process 200, laser (or, alternatively, radio frequency, high frequency ultrasound, or light other than laser light) energy is delivered by the energy delivery device to the tissue adjacent to the distal end of the energy delivery device. In step 230, the catheter and the energy delivery device are slowly retracted along the vein. As the catheter and the energy delivery device are retracted, the energy from the energy delivery device destroys the tissue of the vein.

In one particular embodiment of a catheter in accordance with FIG. 5, the catheter 15" had a lumen 60 with a diameter equal to 6 French gauge or approximately 2.0 mm. The corresponding needle 11" was formed of stainless steel with an outer diameter of 680 microns in the distal end portion 78 of the needle transitioning to an outer diameter of 1.16 mm at a location proximal to the distal end portion. The proximal part 80 of the distal end portion 78 of the needle 11" had its relatively larger radius of curvature R1 equal to approximately 7.8 cm. The distal part 82 of the distal end portion 78 of the needle 11" had its relatively smaller radius of curvature R2 equal to approximately 4.5 cm. The distal part 82 of the distal end portion 78 had a length of approximately 0.3 cm. Stated differently, the part of the needle 11" having a radius of curvature R2 equal to approximately 4.5 cm had an arc length of approximately 0.3 cm, which defined a central angle of approximately 20°. The part of the needle 11" having a radius of curvature R1 equal to approximately 7.8 cm, which included the proximal part 80 of the distal end portion 78, had a length of approximately 4.5 cm. Stated differently, the part of the needle 11" having a radius of curvature R1 equal to approximately 7.8 cm had an arc length of approximately 4.5 cm, which defined a central angle of approximately 26°. In this particular embodiment, the transition in the outer diameter of the needle 11" from 680 microns to 1.16 mm occurred within the curved part of the needle having a radius of curvature R1 equal to approximately 7.8 cm.

When tested, the catheter 15" and needle 11" provided a very pronounced haptic or tactile response as the needle 11" was along the length of the catheter 15" past the openings 16". As the needle 11" was drawn back along the catheter 15" in a proximal direction, the needle reliably and repeatably entered and exited the openings 16". When the needle 11" was moved in the opposite distal direction along the catheter 15", the needle also functioned as intended, but was more difficult for the user to advance or move distally along the catheter than to withdraw or move in the proximal direction.

In another particular embodiment of a catheter in accordance with FIG. 5, the catheter 15" had a lumen 60 with a diameter equal to 4 French gauge or approximately 1.35 mm. The corresponding needle 11" was formed of stainless steel with an outer diameter of 600 microns. The proximal part 80 of the distal end portion 78 of the needle 11" had its relatively larger radius of curvature R1 equal to approximately 7.8 cm. The distal part 82 of the distal end portion 78 of the needle 11" had its relatively smaller radius of curvature R2 equal to approximately 4.5 cm. The distal part 82 of the distal end portion 78 had a length of approximately 0.3 cm. The proximal part 80 of the distal end portion 78 had a length of approximately 4.5 cm.

When tested, the catheter 15" and needle 11" provided a very pronounced haptic or tactile response as the needle 11" was along the length of the catheter 15" past the openings 16". As the needle 11" was drawn back along the catheter 15" in a proximal direction, the needle reliably and repeatably entered and exited the openings 16". When the needle 11" was moved in the opposite distal direction along the catheter 15", the needle also functioned as intended, but was more difficult for the user to advance or move distally along the catheter than to withdraw or move in the proximal direction.

In yet another particular embodiment of a catheter in accordance with FIG. 5, the catheter 15" had a lumen 60 with a diameter equal to 6 French gauge or approximately 2.0 mm. The corresponding needle 11" was formed of stainless steel with an outer diameter of 680 microns transitioning to 1.16 mm. The proximal part 80 of the distal end portion 78 of the needle 11" had its relatively larger radius of curvature R1 equal to approximately 2.5 cm. The distal part 82 of the distal end portion 78 of the needle 11" had its relatively smaller radius of curvature R2 equal to approximately 0.6 cm. The distal part 82 of the distal end portion 78 had a length of approximately 0.1 cm. Stated differently, the part of the needle 11" having a radius of curvature R2 equal to approximately 0.6 cm had an arc length of approximately 0.1 cm, which defined a central angle of approximately 16°. The proximal part 80 of the distal end portion 78 had a length of approximately 1.5 cm. Stated differently, the part of the needle 11" having a radius of curvature R1 equal to approximately 2.5 cm had an arc length of approximately 1.5 cm, which defined a central angle of approximately 30°.

When tested, the catheter 15" and needle 11" provided a more than adequate haptic or tactile response as the needle 11" was along the length of the catheter 15" past the openings 16". (The haptic or tactile response was, however, less pronounced than the response obtained with the previously described embodiment having a catheter 15" with a 6 French diameter lumen 60 and a needle 11" with a 680 micron outer diameter and radii of curvature R1 equal to approximately 7.8 cm and R2 equal to approximately 4.5 cm.) As the needle 11" was drawn back along the catheter 15" in a proximal direction, the needle reliably and repeatably entered and exited the openings 16". When the needle 11" was moved in the opposite distal direction along the catheter 15", the needle also reliably and repeatably entered and exited the openings 16" without difficulty. (The ease of movement of the needle 11" in the distal direction was markedly better than the ease of movement of the needle in the distal direction obtained with the previously described embodiment having a catheter 15" with a 6 French diameter lumen 60 and a needle 11" with a 680 micron outer diameter and radii of curvature R1 equal to approximately 7.8 cm and R2 equal to approximately 4.5 cm.)

The three particular embodiments described above are intended for use with veins having a diameter in a range from about 5 mm to about 11 mm. For blood vessels or other hollow organs with larger internal diameters, the diameters of the catheter 15" and the needle 11" would be relatively larger. It was also observed that stainless steel needles with dual curves and an outer diameter of 600 microns had sufficient column strength to pierce the tissue of a vein successfully, while needles formed of nitinol with a single curve and an outer diameter of 440 microns did not have sufficient column strength. Further, it was observed that a needle with dual curves produced a more abrupt movement of the distal end portion of the needle than a needle with a single curve. This abrupt snapping action of the needle with dual curves produced a haptically perceptible movement of the distal end portion of the needle that was more readily felt or perceived at the proximal end portion of the needle. It is hypothesized that energy stored in the deflected distal part of the distal end portion of such a dual-curve needle, which distal part has the smaller radius of curvature, is more completely or fully released than the energy stored in the deflected distal end portion of a single-curve needle when the tip of the needle moves over the edge of an opening in the catheter wall. The more complete release of the stored energy, it is hypothesized, produces a stronger or more abrupt movement of the distal part of the distal end portion of a dual-curve needle.

While the curved needles 11" of the three particular embodiments described above have been characterized in terms of their respective radii of curvature and arc lengths, they can also be characterized in terms of the angles between lines drawn tangent to various points on the needles. More specifically, with reference to FIG. 5A, for each needle 11" having R1 equal to approximately 7.8 cm and R2 equal to approximately 4.5 cm, a line T1 drawn tangent to the distal end of the curve with radius of curvature R2 intersects a line L1 extending from the non-curved portion of the needle at an angle $\theta 1$ of approximately $57°$, measured on the distal side of the intersection between the lines. A line T2 drawn tangent to the distal end of the curve with radius of curvature R1 intersects the line T1 drawn tangent to the distal end of the curve with radius of curvature R2 at an angle $\theta 2$ of approximately $322°$, measured on the distal side of the intersection between the lines.

Similarly, for the needle 11" having R1 equal to approximately 2.7 cm and R2 equal to approximately 0.6 cm, a line T1 drawn tangent to the distal end of the curve with radius of curvature R2 intersects a line L1 extending from the non-curved portion of the needle at an angle $\theta 1$ of approximately $400°$, measured on the distal side of the intersection between the lines. A line T2 drawn tangent to the distal end of the curve with radius of curvature R1 intersects the line T1 drawn tangent to the distal end of the curve with radius of curvature R2 at an angle $\theta 2$ of approximately $155°$, measured on the distal side of the intersection between the lines. The numerical values set forth above and other numerical values set forth in the present application are given by way of example only and other values may be used with satisfactory results.

The line L1 described above may be the central longitudinal axis 86 of the non-curved, major portion of the needle 11". The non-curved, major portion of the needle 11" is the portion that is substantially straight as manufactured, and thus the longitudinal axis 86 is also substantially straight. Because the distal end portion 78 of the needle 11" is formed with the two radii of curvature R1 and R2, the distal end portion normally extends in a direction away from the proximal end portion (not shown) of the needle and also away from the substantially straight central longitudinal axis 86. More specifically, the proximal part 80 of the distal end portion 78 extends from the axis 86 in a first direction, and the distal part 82 of the distal end portion extends away from the axis 86 in a second direction that is different than the first direction. When the distal end portion 78 of the needle 11" is received in the lumen 60, the catheter wall 19" deflects the distal end portion from its normal curved configuration and toward the axis 86. The catheter wall 19" constrains the distal end portion 78 in a generally straight configuration (shown in dashed lines in FIG. 5). As is also shown in FIG. 5, the axis 86 is substantially coincident with the longitudinal axis 61 of the lumen 60.

As yet another alternative, the needles 11 and 11", which are deployed from inside the catheter walls 19 and 19", respectively, can be replaced with one or more needles that are deployed from outside of a catheter wall. FIGS. 6 and 6A illustrate a catheter assembly 300, in accordance with a fourth embodiment of the present invention. The catheter assembly 300 includes a sheath or catheter 302, which is made of a flexible and resilient bio-compatible material, such as a medical grade elastomer. The catheter 302 includes a catheter wall 304 and a lumen 306 extending lengthwise of the catheter wall.

The catheter wall 304 includes a radially outer surface 308 and a radially inner surface 310. The inner surface 310 at least partially defines the lumen 306. The outer surface 308 and the inner surface 310 are free of ports or openings that extend from the outer surface to the inner surface. The outer surface 308 does, however, include a longitudinally extending groove 312. The inner surface 310 and the lumen 306 both extend substantially the entire length of the catheter 302 and the catheter wall 304.

The lumen 306 is open at both its distal end and its proximal end. The lumen 306 receives an elongated energy delivery device 314. The energy delivery device 314 is a flexible optical fiber that delivers laser energy. At its proximal end, the energy delivery device 314 is connected to an energy source (not shown), which is a source of laser energy. The energy delivery device 314 may alternatively be, for example, a metal wire that delivers radio frequency energy. If the energy delivery device 314 delivers radio frequency energy, the energy source is a source of radio frequency energy. As further alternatives, the energy delivery device 314 may constructed to deliver energy in the form of high frequency ultrasound or light other than laser light, and the energy source may be a source of energy in the form of high frequency ultrasound or light other than laser light, respectively.

An annular, inflatable balloon 316 encircles the catheter 302 and the catheter wall 304. The balloon 316 is attached adjacent its radially inner surface to an annular collar 318, which also encircles the catheter 302 and the catheter wall 304. An opening 320 is formed in the collar 318 and receives one end of an elongated hypotube 322. The other end of the hypotube 322 is connected to a reservoir (not shown) of fluid. The fluid may be a diagnostic fluid, a therapeutic fluid, and/or a fluid to aid in the delivery of energy by, for example, acting as a heat sink. As one example, the fluid may be a tumescent fluid comprising saline solution combined with an anesthetic agent, such as lidocaine. Most of the length of the hypotube 322 is received in the groove 312 in the outer surface 308 of the catheter wall 304. Needles 324, one of which is shown in each of FIGS. 6 and 6A, are spaced apart in a circumferential array along the outer surface of the balloon 316. The needles 324 are hollow and communicate with the interior volume 326 of the balloon 316. The needles 324 are made of a biocompatible material, such as stainless steel, nitinol or polytetrafluoroethylene ("PTFE"), that has sufficient rigidity to penetrate a patient's tissue. The distal tips of the needles 324 can penetrate tissue of a vein 328 and tissue surrounding the vein. As a result of the construction of the needles 324 and the balloon 316, fluid may flow from the fluid reservoir (not shown), through the hypotube 322, into the interior volume 326 of the balloon, and then out of the distal tips of the needles.

In use, the catheter assembly 300 is inserted into a patient's vein 328. The balloon 316 and collar 318 are disposed adjacent the distal end of the catheter 302. The balloon 316 is in a deflated condition, as shown in solid lines in FIGS. 6 and 6A, with the needles 324 pointed in a radially inward direction into the interior volume 326 of the balloon. When the needles 324 are disposed adjacent the most distal portion of the vein 328 to be treated, tumescent fluid is introduced under pressure into the hypotube 322. The pressurized tumescent fluid flows into the interior volume 326 of the balloon 316 and inflates the balloon. As the balloon 316 inflates, the needles 244 are inverted so as to point radially outward and are brought into contact with the tissue of the vein 328. As the balloon 316 continues to inflate, the needles 324 are pressed radially outward into adjacent tissue, which will include both the tissue of the vein 328 and tissue surrounding the vein. As the needles 324 are penetrating the adjacent tissue, the pressured tumescent fluid is introduced into the tissue through the needles.

After a predetermined amount of fluid has been introduced into the tissue adjacent the distal end of the catheter 302, the user of the catheter assembly 300 can move the balloon 316 along the catheter to the next position at which fluid will be introduced into the adjacent tissue. To move the balloon 316 toward the proximal end (not shown) of the catheter 302, the pressure in the hypotube 322 and the balloon is reduced so that the needles 324 are withdrawn from the adjacent tissue and, potentially, inverted to point in a radially inward direction. After the needles 324 are appropriately positioned, the hypotube 322 is pulled in a proximal direction along the groove 312 in the outer surface 308 of the catheter wall 304. The axial movement of the hypotube 322 moves the collar 318, which is attached to the hypotube, and the balloon 316 in a direction toward the proximal end (not shown) of the catheter 302.

When the balloon 316 and the needles 324 are disposed adjacent the next most distal portion of the vein 328 to be treated, the pressure of the tumescent fluid in the hypotube 322 is again increased to inflate the balloon and cause the needles to point radially outward. As the balloon 316 continues to inflate, the needles 324 are pressed radially outward into adjacent tissue. The pressured tumescent fluid is introduced into the tissue through the needles 324.

After a predetermined amount of pressurized tumescent fluid has been introduced into the adjacent tissue, the user of the catheter assembly 300 can resume moving the balloon 316 lengthwise toward the proximal end (not shown) of the catheter 15". In particular, the pressure in the hypotube 322 and the balloon is reduced so that the needles 324 are withdrawn from the adjacent tissue and, potentially, inverted to point in a radially inward direction. With the needles 324 appropriately positioned, the hypotube 322 is pulled in a proximal direction along the groove 312 in the outer surface 308 of the catheter wall 304. The axial movement of the hypotube 322 moves the collar 318, which is attached to the hypotube, and the balloon 316 in a direction toward the proximal end (not shown) of the catheter 302.

The user of the catheter assembly 300 can repeat the above described movements as the balloon 316 is moved lengthwise toward the proximal end (not shown) of the catheter 302 and the needles 324 are correspondingly moved to positions that are increasingly farther from the distal end of the lumen 60. The above described movements may be repeated as many times as may be desired or required to introduce fluid into a length of vascular and/or other tissue that is selected by the user of the catheter assembly 300 either before or after introducing the catheter assembly into the patient's vein 328. After fluid has been introduced into a desired length of vascular and/or other tissue adjacent the catheter assembly 300, the distal end of the energy delivery device 314 is moved to a position at or beyond the distal end of the catheter 302 and the lumen 60, if the energy delivery device is not already in such a position.

Laser (or, alternatively, radio frequency, high frequency ultrasound, or light other than laser light) energy is then delivered by the energy delivery device 314 to the tissue adjacent to the distal end of the energy delivery device. The catheter 302 and the energy delivery device 314 are slowly retracted together along the vein 328. As the catheter 302 and the energy delivery device 314 are retracted, the energy from the energy delivery device destroys the tissue of the vein 328. During the foregoing treatment process, the fluid that has previously been injected into the patient's tissue acts as a heat sink so that tissue around the vein 328 tends not to be affected by heat produced by the delivery of energy via the energy delivery device 314. The fluid also constricts the vein from outside the vein 328 so that treatment of the vein tends to be more effective, and anesthetic in the fluid helps numb any sensation of pain. As a result of the treatment process, the vein 328 collapses and is eventually absorbed by the patient's body.

Although the needles 11 and 11' of the catheter assemblies 10 and 10" are illustrated in FIGS. 1-2 and 4, respectively, and described as being received in a catheter 15 having two lumens 17 and 18, the needles 11 and 11' could alternatively be used with and received in a catheter 15" with a single 60, as shown in FIG. 5. Similarly, the needle 11" of the catheter assembly 10", which is illustrated in FIG. 5 and described as being received in a catheter 15" having a single lumen 60, could alternatively be used with and received in a catheter 15 with two lumens 17 and 18, as shown in FIGS. 1-2 and 4.

In addition, while the catheter assemblies 10, 10', and 10" are expected to be held by a user so that movement of the proximal end portion of the needle will be haptically perceived by the user through his or her hands, the movement could additionally or alternatively be detected via a sensor. Connecting the output of such a sensor to a visual communication device, such a CRT, LCD, or LED display, or to an audible communication device, such as a speaker, could provide confirmatory information to the user of the catheter assembly 10, 10', or 10" or allow a skilled user to train or provide remote guidance to a less skilled user who is actually holding and manipulating the catheter assembly.

As described above, the catheter assemblies 10, 10', 10", and 200 are used in the treatment of vascular disease, particularly varicose veins. Nonetheless, the catheter assemblies 10, 10', 10", and 200 could be used in the treatment of any hollow anatomical structure. More specifically, the catheter assemblies 10, 10', 10", and 200 could be used to deliver fluid to tissue that surrounds and defines a lumen within any body organ.

From the above description of the invention, those skilled in the art will perceive improvements, changes and modifications. Such improvements, changes, and/or modifications within the skill of the art are intended to be covered by the appended claims.

Having described the invention, the following is claimed:

1. A method of delivering fluid to tissue surrounding a lumen of a body organ comprising the steps of:
   inserting into the lumen of the body organ a catheter assembly that includes a catheter and an elongated hollow needle with a proximal end portion and a distal end portion, the catheter including a catheter wall and a catheter lumen extending lengthwise of the catheter wall, the catheter wall having a radially inner surface and a radially outer surface, the catheter wall including a plurality of openings that extend through the catheter wall from the inner surface to the outer surface, the openings communicating with the catheter lumen, the distal end portion of the needle being directed radially outward so as to extend into an adjacent one of the openings, the distal end portion having a configuration that stores potential energy when the distal end portion is disposed within the catheter lumen, the potential energy being converted to kinetic energy to produce movement of the distal end portion of the needle and thereby to produce movement of the proximal end portion in response to such movement of the distal end portion as the distal end portion moves from the inner surface of the catheter wall across the edge of and into said adjacent one of the openings, the movement of the proximal end portion being haptically perceptible;
   moving the needle lengthwise in the catheter lumen so that the distal end portion moves along the inner surface of the catheter wall until the distal end portion of the needle is disposed adjacent an edge of a first one of the plurality of openings;
   continuing to move the needle lengthwise in the catheter lumen so that the distal end portion of the needle moves from the inner surface of the catheter wall across the edge of and into the first one of the plurality of openings to convert stored potential energy in the distal end portion of the needle to kinetic energy so as to produce radially outward movement of the distal end portion of the needle as the distal end portion moves from the inner surface of the catheter wall into the first one of the plurality of openings and thereby to produce haptically perceptible movement of the proximal end portion of the needle in response to such radially outward movement of the distal end portion;
   extending the distal end portion of the needle into a first portion of tissue outside of the lumen in the body organ by moving the needle lengthwise in the catheter lumen upon haptically perceiving the movement of the proximal end portion of the needle in response to the radially outward movement of the distal end portion;
   introducing a fluid into the first portion of tissue through the hollow needle;
   retracting the distal end portion of the needle from the first portion of tissue and into the catheter lumen by moving the needle lengthwise in the catheter lumen;
   moving the needle lengthwise in the catheter lumen so that the distal end portion moves along the inner surface of the catheter wall until the distal end portion of the needle is disposed adjacent an edge of a second one of the plurality of openings;
   continuing to move the needle lengthwise in the catheter lumen so that the distal end portion of the needle moves from the inner surface of the catheter wall across the edge of and into the second one of the plurality of openings to convert stored potential energy in the distal end portion of the needle to kinetic energy so as to produce radially outward movement of the distal end portion of the needle as the distal end portion moves from the inner surface of the catheter wall into the second one of the plurality of openings and thereby to produce haptically perceptible movement of the proximal end portion of the needle in response to such radially outward movement of the distal end portion;
   extending the distal end portion of the needle into a second portion of tissue outside of the lumen in the body organ by moving the needle lengthwise in the catheter lumen upon haptically perceiving the movement of the proximal end portion of the needle in response to the radially outward movement of the distal end portion;
   introducing the fluid into the second portion of tissue through the hollow needle; and
   retracting the distal end portion of the needle from the second portion of tissue and into the catheter lumen by moving the needle lengthwise in the catheter lumen.

2. A method according to claim 1 further comprising the steps of (a) inserting an energy delivery device into the catheter and (b) applying energy to the body organ through the energy delivery device.

3. A method according to claim 1 wherein the steps of moving the needle in the catheter lumen, moving the distal end portion of the needle, extending the distal end portion of the needle, introducing fluid into tissue, and retracting the distal end portion of the needle are repeated for each of a predetermined number of openings.

4. A method according to claim 1 wherein the configuration of the distal end portion of the needle includes a first radius of curvature for a curved first part of the distal end portion and a second radius of curvature for a curved second part of the distal end portion.

5. A method according to claim 4 wherein the second part of the distal end portion is located distally of the first part of the distal end portion, the second radius of curvature being smaller than the first radius of curvature.

6. A method according to claim 5 wherein the first part of the distal end portion has a first length and the second part of the distal end portion has a second length, the second length being smaller than the first length.

7. A method according to claim 1 wherein the distal end portion of the needle extends away from a substantially straight portion of the needle that has a substantially straight central longitudinal axis, the configuration of the distal end portion including a first part of the distal end portion extending away from the substantially straight central longitudinal axis in a first direction different from the substantially straight central longitudinal axis and a second part of the distal end portion extending away from the substantially straight central longitudinal axis in a second direction different from the first direction and different from the substantially straight central longitudinal axis.

8. A method according to claim 7 wherein the second part of the distal end portion extends away from the substantially straight central longitudinal axis in a curve and is located distally of the first part of the distal end portion.

9. A method according to claim 8 wherein the first part of the distal end portion has a first length and the second part of the distal end portion has a second length, the second length being smaller than the first length.

10. A method according to claim 1 wherein the configuration of the distal end portion includes a first configuration for a first part of the distal end portion and a second configuration for a second part of the distal end portion, the second configuration being a curve, the second part of the distal end portion being located distally of the first part of the distal end portion.

11. A method according to claim 10 wherein the first part of the distal end portion has a first length and the second part of the distal end portion has a second length, the second length being smaller than the first length.

12. A method according to claim 1 wherein the configuration of the distal end portion is predetermined, the distal end portion being resilient in a radial direction so that when the distal end portion is resiliently deflected from the predetermined configuration by the catheter wall, the distal end portion is resiliently biased to return to the predetermined configuration and extend into said adjacent one of the openings.

13. A method according to claim 1 wherein the catheter has only a single catheter lumen.

14. A method according to claim 1 wherein the method is a method of treating a vascular disease, the body organ being a blood vessel.

15. A method according to claim 1 wherein the step of continuing to move the needle lengthwise in the catheter lumen so that the distal end portion of the needle moves from the inner surface of the catheter wall across the edge of and into the first one of the plurality of openings includes locating the first one of the plurality of openings by moving the distal end portion of the needle from the inner surface of the catheter wall across the edge of and into the first one of the plurality of openings to produce radially outward movement of the distal end portion of the needle, the step of continuing to move the needle lengthwise in the catheter lumen so that the distal end portion of the needle moves from the inner surface of the catheter wall across the edge of and into the second one of the plurality of openings including locating the second one of the plurality of openings by moving the distal end portion of the needle from the inner surface of the catheter wall across the edge of and into the second one of the plurality of openings to produce radially outward movement of the distal end portion of the needle.

16. A method according to claim 1 wherein the steps of moving the needle in the catheter lumen, continuing to move the needle in the catheter lumen, and retracting the distal end portion of the needle are movements of the needle in a first longitudinal direction lengthwise of the catheter, the steps of extending the distal end portion of the needle by moving the needle lengthwise in the catheter lumen are movements of the needle in a second longitudinal direction opposite the first longitudinal direction.

* * * * *